United States Patent [19]

Hollister

[11] Patent Number: 4,982,842
[45] Date of Patent: Jan. 8, 1991

[54] SAFETY NEEDLE CONTAINER

[75] Inventor: William H. Hollister, Keene, N.H.

[73] Assignee: Concord/Portex, Keene, N.H.

[21] Appl. No.: 532,558

[22] Filed: Jun. 4, 1990

[51] Int. Cl.$^5$ .......................... A61M 5/32; A61M 5/00
[52] U.S. Cl. .................................. 206/365; 604/192;
604/198; 604/263
[58] Field of Search ................ 206/365; 604/192, 198,
604/263

[56] References Cited

U.S. PATENT DOCUMENTS

| 1,779,451 | 10/1930 | Sponsel . |
| 2,700,385 | 1/1955 | Ortiz . |
| 2,836,942 | 6/1958 | Miskel . |
| 2,854,976 | 10/1958 | Heydrich . |
| 2,953,243 | 9/1960 | Roehr . |
| 3,021,942 | 2/1962 | Hamilton . |
| 3,073,307 | 1/1963 | Stevens . |
| 3,074,542 | 1/1963 | Myerson et al. . |
| 3,255,873 | 6/1966 | Speelman . |
| 3,294,231 | 12/1966 | Vanderbeck . |
| 3,323,523 | 6/1967 | Scislowicz et al. . |
| 3,329,146 | 7/1967 | Waldman, Jr. . |
| 3,333,682 | 8/1967 | Burke . |
| 3,367,488 | 2/1968 | Hamilton . |
| 3,485,239 | 12/1969 | Vanderbeck . |
| 3,537,452 | 11/1970 | Wilks . |
| 3,610,240 | 10/1971 | Harautuneian . |
| 3,658,061 | 4/1972 | Hall . |
| 3,828,775 | 8/1974 | Armel . |
| 3,890,971 | 6/1975 | Leeson et al. . |
| 3,904,033 | 9/1975 | Haerr . |
| 3,934,722 | 1/1976 | Goldberg . |
| 3,968,876 | 7/1976 | Brookfield . |
| 4,113,090 | 9/1978 | Carstens . |
| 4,139,009 | 2/1979 | Alvarez . |
| 4,175,008 | 11/1979 | White . |
| 4,300,678 | 11/1981 | Gyure et al. . |
| 4,375,849 | 3/1983 | Hanifl . |
| 4,430,082 | 2/1984 | Schwabacher . |
| 4,592,744 | 6/1986 | Jagger et al. . |
| 4,634,428 | 1/1987 | Cuu . |
| 4,643,722 | 2/1987 | Smith, Jr. . |
| 4,659,330 | 4/1987 | Nelson et al. . |
| 4,664,259 | 5/1987 | Landis .................................. 206/36.5 |
| 4,664,654 | 5/1987 | Strauss . |
| 4,681,567 | 7/1987 | Masters et al. . |
| 4,695,274 | 9/1987 | Fox . |
| 4,702,738 | 10/1987 | Spencer . |

(List continued on next page.)

FOREIGN PATENT DOCUMENTS 1233302  5/1971  United Kingdom .
87/07162 12/1987 World Int. Prop. O. .

Primary Examiner—William I. Price
Attorney, Agent, or Firm—Pollock, Vande Sande & Priddy

[57] ABSTRACT

A universal safety adapter which is usable with different types of needles and syringes has integral first and second sections and a housing flexibly connected to one of the sections. In the case of the first section being adaptable to be mated with the hub of a needle assembly, the housing is flexibly connected thereto by way of a living hinge. The needle assembly is threadedly mated with an internally threaded annular collar surrounding a protrusion which is to be coupled to the hub of the needle assembly. The second section of the safety adapter, in a first embodiment, includes a female luer that is adaptable to be mated with different types of syringes, such as a luer slip syringe or a luer lock syringe. Once the needle assembly has been threadedly mated to the first section of the safety adapter, to ensure that the cannula of the needle assembly is not exposed so as to preclude accidental pricking by the needle, the housing is pivoted to a position whereby it completely envelops the cannula. At least one integral retainer mechanism in the housing prevents relative movement between the cannula and the housing once the housing has been pivoted to envelop the cannula. The dead space volume at the junction where the needle is connected to the syringe can be substantially reduced by a second embodiment of the safety adapter of the present invention which includes a male extension within the female luer.

27 Claims, 3 Drawing Sheets

4,982,842

Page 2

U.S. PATENT DOCUMENTS

| | | |
|---|---|---|
| 4,723,943 | 2/1988 | Spencer. |
| 4,728,320 | 3/1988 | Chen. |
| 4,728,321 | 3/1988 | Chen. |
| 4,731,059 | 3/1988 | Wanderer et al.. |
| 4,735,311 | 4/1988 | Lowe et al.. |
| 4,735,618 | 4/1988 | Hagan. |
| 4,737,144 | 4/1988 | Choksi. |
| 4,738,663 | 4/1988 | Bogan. |
| 4,743,233 | 5/1988 | Schneider. |
| 4,747,836 | 5/1988 | Luther. |
| 4,747,837 | 5/1988 | Hauck. |
| 4,772,272 | 9/1988 | McFarland. |
| 4,778,453 | 10/1988 | Lopez. |
| 4,781,697 | 11/1988 | Slaughter. |
| 4,782,841 | 11/1988 | Lopez. |
| 4,790,828 | 12/1988 | Dombrowsk et al.. |
| 4,795,432 | 1/1989 | Karczmer. |
| 4,795,443 | 1/1989 | Permenter et al.. |
| 4,801,295 | 1/1989 | Spencer. |
| 4,804,372 | 2/1989 | Laico et al.. |
| 4,813,426 | 3/1989 | Haber et al.. |
| 4,816,022 | 3/1989 | Pancy. |
| 4,816,024 | 3/1989 | Sitar et al.. |
| 4,819,659 | 4/1989 | Sitar. |
| 4,820,277 | 4/1989 | Norelli. |
| 4,826,490 | 5/1989 | Byrne et al.. |
| 4,826,491 | 5/1989 | Schramm. |
| 4,838,871 | 6/1989 | Luther. |
| 4,842,587 | 6/1989 | Poncy. |
| 4,846,796 | 7/1989 | Carrell et al.. |
| 4,850,968 | 7/1989 | Romano. |
| 4,850,976 | 7/1989 | Heinrich et al.. |
| 4,850,977 | 7/1989 | Bayless. |
| 4,850,978 | 7/1989 | Dudar. |
| 4,850,994 | 7/1989 | Zerbst et al.. |
| 4,850,996 | 7/1989 | Cree. |
| 4,858,607 | 8/1989 | Jordan et al.. |
| 4,863,434 | 9/1989 | Bayless. |
| 4,863,435 | 9/1989 | Sturman et al.. |
| 4,863,436 | 9/1989 | Glick. |
| 4,867,746 | 9/1989 | Dufresne. |
| 4,872,552 | 10/1989 | Unger. |
| 4,874,383 | 10/1989 | McNaughton. |
| 4,874,384 | 10/1989 | Nunez. |
| 4,883,469 | 11/1989 | Glazier. |
| 4,886,503 | 12/1989 | Miller. |
| 4,888,001 | 12/1989 | Schoenberg. |
| 4,892,107 | 1/1990 | Haber. |
| 4,892,521 | 1/1990 | Laico et al.. |
| 4,900,309 | 2/1990 | Netherton et al.. |
| 4,927,018 | 5/1990 | Yang et al. .......................... 206/365 |
| 4,944,397 | 7/1990 | Miller .................................. 206/365 |

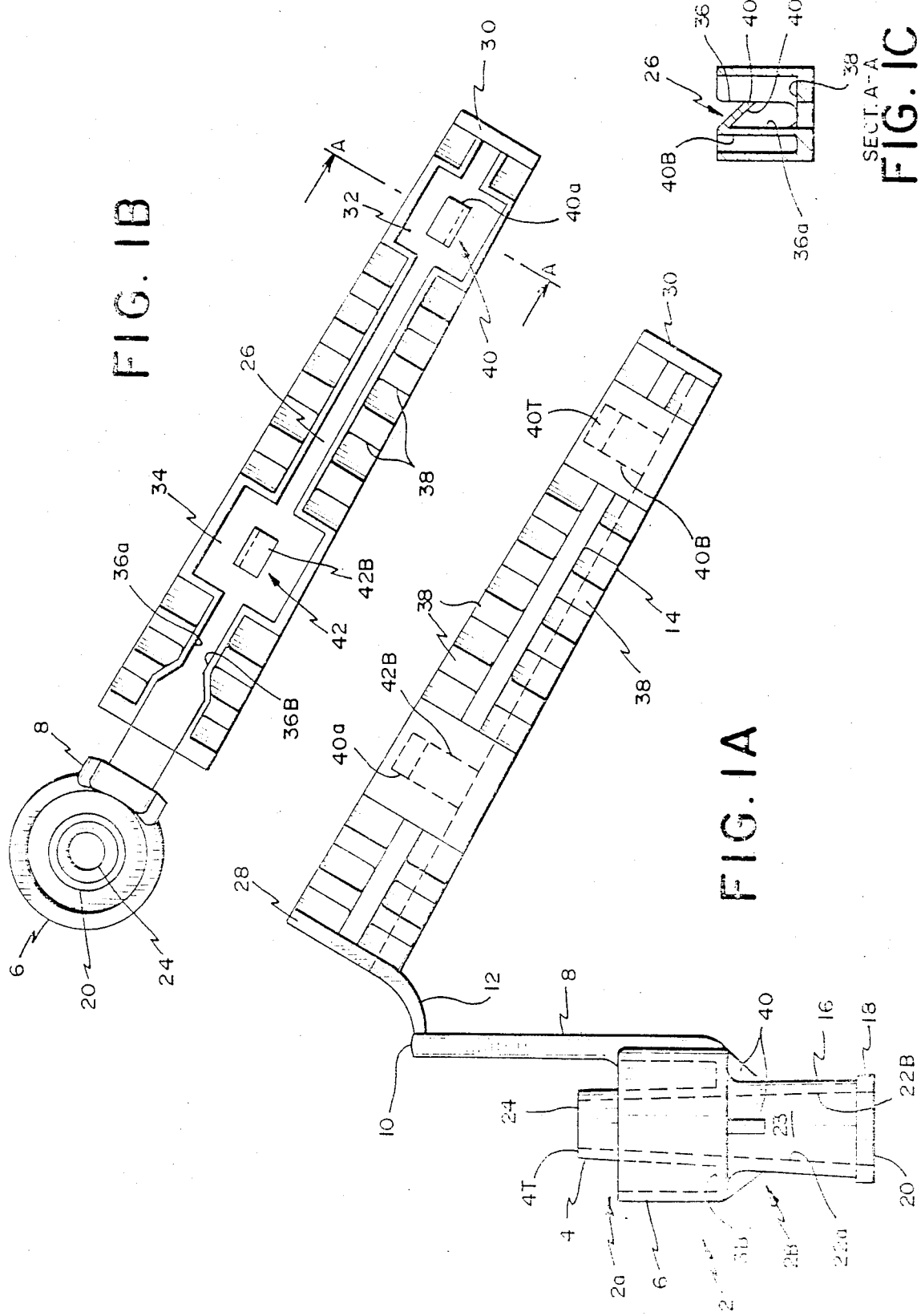

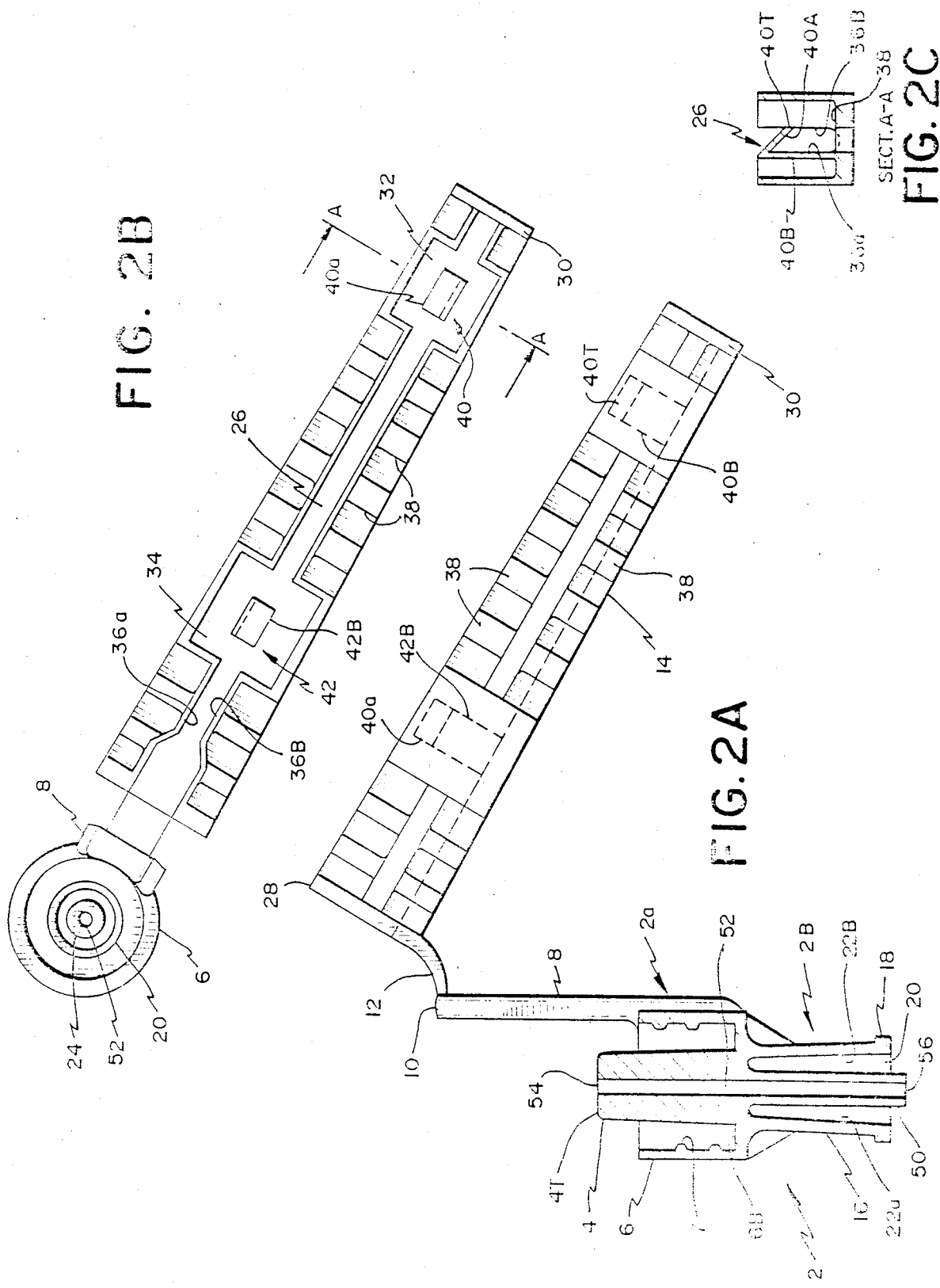

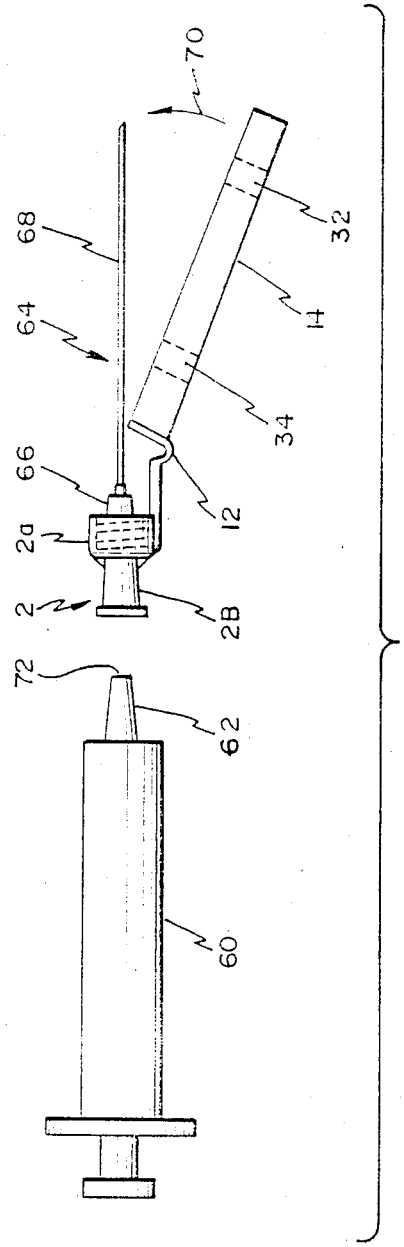
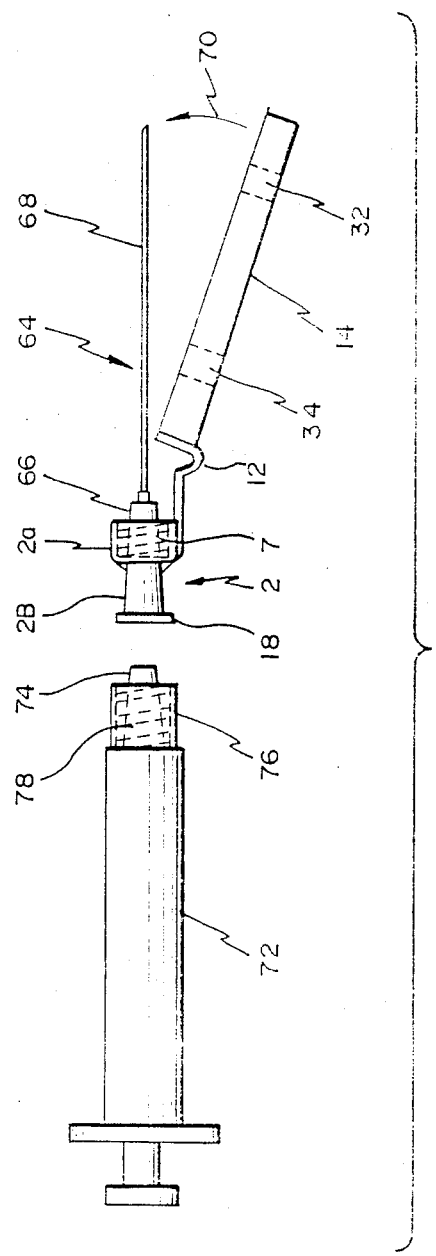

SAFETY NEEDLE CONTAINER

FIELD OF THE INVENTION

This invention is related to hypodermic needles and more particularly to a safety device for housing a hypodermic needle such that a person will not be accidently pricked by the needle, particularly after the needle has been used and is to be disposed of.

BACKGROUND OF THE INVENTION

In handling a hypodermic needle, there is always a chance that the user, or persons in the proximity of the needle, may be exposed to accidental pricking thereby. And in view of the current crop of infectious diseases, particularly the as yet incurable Acquired Immune Deficiency Syndrome (AIDS), an urgent need exists to provide a safety device for preventing accidental pricking by a needle, especially one that has been used and is therefore contaminated There are in the prior art a number of safety devices for guarding a needle, or more precisely its cannula, so that its sharp end will not be exposed For example, Sponsel U.S. Pat. No. 1,779,451 discloses a syringe that has a needle guide pivotable at a point about the syringe casing for guarding the needle. Scislowicz U.S. Pat. No. 3,323,523 discloses a sheath formed of two portions that can pivot about respective hinges to cover a cannula. Moreover, the sheath may be locked by having a sleeve slid thereover. Hall U.S. Pat. No. 3,658,061 discloses a catheter needle guard unit that may be pivoted to snap over the needle. The sheath, once snapped, may be unsnapped since it is not locked onto the needle. Smith, Jr. U.S. Pat. No. 4,643,722 discloses a hypodermic needle assembly that has a closure having an elongated slot which enables the closure to be either removed from or inserted toward the hypodermic needle. The Smith device requires two-handed operation. Furthermore, no locking means is disclosed. Nelson et al. U.S. Pat. No. 4,659,330, on the other hand, discloses a needle protective cap which is slidable, by means of a clip, along the body of the syringe. The needle cover, however, may be completely removed from the needle.

Additional slidable needle protectors are disclosed in Spencer U.S. Pat. No. 4,702,738 and 4,723,943 wherein a protective sheath is shown to be slidable along a syringe body. Yet other needle covers that are slidable along a syringe body are disclosed in Choksi U.S. Pat. No. 4,737,144 and Schneider U.S. Pat. No. 4,743,233. Some other example devices having protective sheaths for needles include Laico et al. U.S. Pat. No. 4,804,372; Poncy U.S Pat. No. 4,816,022; Schramm U.S. Pat. No. 4,826,491; Poncy U.S. Pat. No. 4,842,587; Carrell et al. U.S. Pat. No. 4,846,796; Romano U.S. Pat. No. 4,850,968; Bayless U.S Pat. No. 4,850,977; Zerbst et al. U.S. Pat. No. 4,850,994; Cree U.S. Pat. No. 4,850,996; Jordan et al. U.S. Pat. No. 4,858,607; Bayless U.S. Pat. No. 4,863,434 and Haber U.S. Pat. No. 4,892,107. As is readily apparent, all of these devices having covers that are slidable along the length of the syringe body require twohanded operation.

Another type of prior art needle protective device involves the pivoting of a needle sheath to cover the cannula of the needle assembly. Some prior art examples of this type of device include Norelli U.S. Pat. No. 4,820,277 wherein a pair of jaws is disclosed as pivotable and lockable over a needle. As is readily apparent, however, the Norelli cover also requires two-handed operation. Glazier U.S Pat. No. 4,883,469 discloses a guard assembly that is coupled to a sheath by a fastener and is rotatable about a hinge to snap onto the needle. The sheath, along with the pivotable guard, has to be preassembled with the needle for a specific type of syringe Schoenberg U.S. Pat. No. 4,888,001 discloses a longitudinal shank having two flat wings which are pivotable to enclose the sharp distal end of the needle. None of these prior art devices apparently discloses the permanent retention of the needle by the protective sheath once the protective sheath has been pivoted to enclose the needle.

There are a couple of prior art safety devices that do teach the permanent retention of a needle within the housing once it has been enclosed thereby Landis U.S Pat. No. 4,664,259 is one such which discloses a needle assembly that includes a pivotable housing having therein a hook to retain the needle within the housing after the housing has been pivoted to enclose the needle. The Landis device, however, comes in a unitary package, inasmuch as the needle is integrated into the base, which in turn has connected thereto the pivotable housing. In Unger U.S. Pat. No. 4,872,552, there is also disclosed a pivotable housing integrated into a needle. In an alternative embodiment, the Unger housing has to be threaded to a specific type of needle housing hub. To lock the housing permanently to the needle, a plug has to be pushed from the top of the housing longitudinally into the housing until the tip of the needle rests within the plug.

Even with the '259 and '552 devices, inasmuch as there is available in the market a number of different types of needles and syringes, there still remains a need to have a universal safety device that is adaptable to be used with the different types of needles and syringes. Moreover, it is imperative that such safety device has to be amendable to single-handed operation, as for example during emergency room situations where a user may have only one hand free.

Moreover, it has been found that oftentimes there is a large unused and therefore wasteful volume of space at the junction where the syringe and needle are joined which has to be filled with blood to be drawn from or fluid to be injected into a patient.

SUMMARY OF THE PRESENT INVENTION

The safety device of the present invention is a stand alone adapter that has a male and female end for mating with a needle assembly and the ejection end of a syringe, respectively. There is flexibly connected to the portion of the adapter that is to be mated with the needle assembly a housing which is pivotable to a position in alignment with the needle for enveloping the same. Integrated within the housing is at least one locking means for permanently retaining the needle within the housing once the housing has been pivoted into the alignment position.

The portion of the adapter to be mated with the needle assembly includes a male luer that is surrounded by an internally threaded annular collar, which is used to mate with the hub of the needle assembly. There is extending from a portion of the annular collar a shoulder member, which has connected to its distal end, by way of a living hinge, the housing. The housing has an elongated slot formed longitudinally along one length thereof. When a needle assembly, via its hub, is threaded into the annular collar so that it is mated with the male luer, the elongated slot would be aligned to face the needle (or cannula) so that the needle would pass therethrough, as the housing is pivoted about the shoulder member to enclose the needle. Integral of the housing is a resilient hook member which gives way to the needle when the housing is pivoted into its alignment position, but which, once the needle is in place, would form a secure fastener for permanently retaining the needle within the housing. With the housing completely enveloping the needle and permanently retaining the same therein, there is no possibility that a person may be accidentally pricked by the needle.

A first embodiment of the safety device of the present invention envisions the end of the adapter that is to be mated to the male luer of the syringe as containing only a female luer, so that the male luer, i.e., the ejection end, of the syringe may be slip-fittedly mated with the adapter. There is disposed at the distal end of the adapter perpendicularly to the longitudinal length of the adapter at least one extension for threadedly locking the female luer of the adapter to the male luer of a syringe if the syringe is a luer lock type syringe that has an internally threaded annular collar surrounding the male luer.

A second embodiment of the adapter of the present invention envisions the use of a male member within the female luer such that the volume of space through which fluid transits between the syringe and the needle is substantially reduced.

To ensure that the present invention safety adapter is adaptable for all types of needles having different lengths, it is further envisioned that a plurality of locking means be integrated into the housing of the adapter.

To operate, after the needle has been used, inasmuch as the housing is flexibly attached to the safety adapter, by pushing against some solid object, the housing can be pivoted about and securely retain the contaminated needle. Thus, the safety adapter of the present invention requires only single-handed operation.

It is, therefore, an objective of the present invention to provide a universal safety adapter that is adaptable to mate with all types of needles and syringes.

It is another objective of the present invention to provide for a safety adapter that does not require two-handed operation.

It is yet another objective of the present invention to provide for a safety adapter that can substantially reduce the volume of dead space through which fluid transits between the syringe and the needle.

The above-mentioned objectives and advantages of the present invention will become more apparent and the invention itself will best understood by reference to the following description of embodiments of the present invention taken in conjunction with the accompanying drawings, wherein:

BRIEF DESCRIPTION OF THE FIGURES

FIG. 1A is a side view of a first embodiment of the present invention safety adapter;

FIG. 1B is a plan view of the FIG. 1A embodiment;

FIG. 1C is a cross-sectional view of section A—A noted in FIG. 1B;

FIG. 2A is a semi-cross sectional view of another embodiment of the safety adapter of the present invention;

FIG. 2B is a plan view of the FIG. 2 embodiment;

FIG. 2C is a cross-sectional view shown along cut A—A in FIG. 2B;

FIG. 3 is an overall view of the safety adapter of the present invention being used with a luer slip type syringe; and FIG. 4 is an overall view of the safety adapter of the present invention being used with a luer lock type syringe.

DETAILED DESCRIPTION OF THE INVENTION

With reference to FIG. 1A, there is shown a safety needle adapter having a base 2 with a first section 2a and a second section 2b. Both sections 2a and 2b are integral of one piece molded base 2.

Section 2a includes a central protrusion 4, conventionally known as a male luer. Surrounding protrusion 4 is an annular collar 6, extending from approximately the midsection of base 2. Collar 6, although not shown as such in FIG. 1A, in practice, is internally threaded, as shown in FIG. 2A. Extending from a portion of collar 6 is a substantially rigid shoulder member 8. Connected to the distal end 10 of shoulder member 8, by way of a living hinge 12, is a housing 14.

Section 2b extends approximately from the midsection of base 2 away from collar 6, as a hub or extension 16. At the distal end of hub 16 is, for this embodiment, a circumferential extension 18, extending orthogonally to the longitudinal length of base 2, for mating with the internal threads of a syringe. It should be appreciated that instead of a ring-like extension, 18 may actually be comprised of a plurality of singular extensions. There is formed at the base of hub 16 an opening 20 which extends in a decreasingly tapered fashion along dotted lines 22a and 22b to the top of protrusion 4 to meet with an opening 24. Conventionally, hub 16 may also be considered as the female luer portion of the adapter of the present invention.

By connecting housing 14 via living hinge 12 to shoulder member 8, housing 14 is pivotable about distal end 10 of shoulder member 8, such that it comes into an alignment position about the longitudinal axis of the cannula (which also happens to be the longitudinal axis of base 2) of a needle assembly, as shown and to be discussed in FIGS. 3 and 4. There is shown in greater detail in FIG. 1B an elongated slot 26 running from base 28 of housing 14 to tip 30 thereof. Tip 30 for this embodiment is solid, but may be hollow for other embodiments. The length of housing 14 is such that it may be used for the longest or shortest, as well as any length in between, needle available in the market.

As shown in FIG. 1B, there is an opening 32 located near tip 30 and another opening 34 located closer to base 28 of housing 14. With reference also to FIG. 1C, it can be seen that slot 26 is bounded by sides 36a and 36b, running substantially in parallel along the length of housing 14, and a base 38. At the center of respective openings 32 and 34 there is integral of housing 14 corresponding hook-like retaining mechanisms 40 and 42. As best shown in FIG. 1C, each of the retaining mechanisms 40 and 42 has a substantially rigid finger 40a extending in a downward slope fashion from the apex of extension 40b, molded to base 38. It should be appreciated that, although substantially rigid, finger 40a may be biased by the cannula of a needle assembly toward extension 40b until the cannula is past tip 40t thereof, at which time finger 40a flexes back into the position shown in FIG. 1C, thereby permanently retaining the cannula within the spaced defined between finger 40a and extension 40b to prevent the cannula from moving relative to housing 14.

Retainer mechanism 42 is the same as retainer mechanism 40 except, as shown in FIG. 1B, its finger portion 42b slopes downward toward side 36b of housing 14. In contrast, finger 40a of retaining mechanism 40 is shown to be sloping downward toward side 36a in the housing. By thus transposing the finger portions of the respective retaining mechanisms, it becomes more difficult for the cannula of the needle assembly to be forcibly removed from the housing, were the cannula being retained by both retaining mechanisms.

To provide strength for the housing, a plurality of ribs 38 is provided along the length of housing 14. Likewise, to provide strength to base 2, a number of buttress ribs 40 slanting upward from hub 16 to base 6b of annular collar 6 is used. These buttress ribs provide rigidity and strength to base 2 such that the latter would not crack even if it were subjected to undue bending moment at base 6b.

A second embodiment of the safety adapter of the present invention is illustrated in FIGS. 2a, 2b and 2c. For these figures, components which are the same as the components shown in FIGS. 1a, 1b and 1c, or perform essentially the same functions, are labeled the same.

Like the first embodiment, the FIG. 2 embodiment also has a base 2 connected, by way a shoulder member 8 and a living flexible hinge 12, to a housing 14. This embodiment, however, is directed to substantially reducing the volume of space through which a fluid—be it blood or medicament—transits between the syringe and the needle, as for example when blood is being drawn from a patient to the syringe or when a medicament in the syringe is being intravenously fed to the patient via the needle.

To achieve this end, the embodiment of FIG. 2A has incorporated into base 2, particularly at section 2b, a conical extension (i.e., a snout or male luer) 50 extending from approximately base 6b to beyond the plane of hole 20 at the base of the adapter. Furthermore, instead of having a through bore such as 23 shown in FIG. 1 extending from top hole 24 to bottom hole 20 and confined by sidewalls 22a and 22b and therefore having a substantial amount of dead space, the FIG. 2A embodiment now has a through bore 52 running continuously from top 4t of male luer 4 at opening 54 to the distal end of conical extension 50, at opening 56. The diameter of through bore 52 is to be manufactured to substantially correspond to the typical bore of a typical needle (cannula) of a needle assembly so that fluid transiting between openings 54 and 56 would flow directly into the bore of the cannula, without having to fill up unnecessary dead space such as shown in FIG. 1A.

The inventor has found that this elimination of dead space, in addition to being attractive to a clinician, in actuality, has the important advantage of not requiring the withdrawal of a larger amount of blood than is necessary, as is done conventionally. To elaborate, ordinarily, for an infant, to withdraw an amount of blood more than is necessary (for example ½ cc) for the requisite tests would be traumatic. Yet, conventionally, a lot more blood than is necessary is in fact withdrawn from the infant, in view of the large amount of dead space between the syringe and the needle, such as exemplified by through bore 23 in FIG. 1A.

With the embodiment shown in FIG. 2A, however, inasmuch as the through bore through which fluid transits has been reduced by conical extension 50, acting effectively as a male extension within female luer 16 at section 2b of base 2, only a minimal necessary amount of blood needs to be drawn. It should be appreciated that the length of conical extension 50 in section 2b, and the length of male luer 4 in section 2a, may be longer or shorter than the respective lengths illustrated in FIG. 2B. Likewise, the length of shoulder member 8 may be lengthened or shortened, so long as it enables housing 14, when pivoted to align along and about the longitudinal axis of the cannula, to be cleared of the hub of the needle assembly to which the cannula is attached.

In operation, with reference to FIGS. 3 and 4, it can be seen that either embodiment of the safety adapter of the instant invention may be mated to a luer slip syringe 60, shown in FIG. 3, that has as its ejection end a male luer 62. For the FIG. 3 illustration, assuming that the safety adapter embodiment shown in FIG. 1A is used, the user needs only to slip-fittedly insert male luer 62 into female luer 2b of base 2 for mating. Needle assembly 64, in the meanwhile, is threaded, by means of its hub 66, into annular collar 6. The female luer portion of hub 66 of needle assembly 64 is therefore mated to male luer 4 of base 2, best shown in FIG. 1A. Cannula 68 of needle assembly 64, after use, can be prevented from being exposed and accidentally pricking a person by pivoting housing 14, via living hinge 12 following directional arrow 70, to envelope cannula 68.

As should be readily apparent, when housing 14 is pivoted to align along the longitudinal axis of cannula 68, retaining mechanisms 40 and 42 (see FIGS. 1a and 1b), upon closing of housing 14 onto cannula 68, will securely retain cannula 68 housing 14 so that there is no relative movement between housing 14 and cannula 68. It should further be appreciated that, as the length of cannula 68 varies, the fact that there is a plurality of retaining mechanisms integral of housing 14 ensures that the cannula would be retained therein. Alternatively, it should further be appreciated that in place of a plurality of retaining mechanisms, only one retaining mechanism, appropriately positioned somewhere along the length of housing 14, may be used. The relative positioning of the retaining mechanisms along housing 14 is determined, of course, to a great extent, by the envisioned length of the to be used cannula.

For the FIG. 3 illustration, if the embodiment of the safety adapter of FIG. 2A is to be used in place of that shown in FIG. 1A, the same slip-fit mating of male luer 62 and female luer 2b discussed earlier remains true. But in addition to that, conical extension (male luer) 50 within female luer 2b of base 2 (See FIG. 2A) is now inserted through hole 72 into male luer 62 of syringe 60. And inasmuch as through bore 52 (see FIG. 2A) has substantially the same diameter as the bore of cannula 68 and thus in effect provides a direct path from syringe 60 into hub 66 of needle assembly 64, the volume of space through which a fluid transits between syringe 60 and cannula 68 is substantially reduced. In other words, the dead space volume in a conventional connection between the hub of a needle assembly and the male luer of a syringe is substantially reduced.

In FIG. 4, there is shown a luer lock type syringe 72 which has an internally threaded collar 76 surrounding its male luer 74. The mating of hub 66 of needle assembly 64 to section 2a of base 2 is as was discussed with reference to FIG. 3 and therefore will not be further discussed herein. As for the mating of section 2b to male luer 74, with the addition of annular collar 76, extension 18 at the distal end of section 2*b* (See FIG. 2A) is now used to threadedly mate with thread 78 at the inner circumference of collar 76. Male luer 74 of course will remain slip-fittedly mated with section 2*b*, if the safety adapter shown in FIG. 1A is used. If, instead, the safety adapter shown in FIG. 2A is used, then in addition to slip fitting along sides 22*a* and 22*b* (see FIG. 2A) of section 2*b*, the interior of male luer 74 will also be mated with conical extension 50 so that dead space volume will be reduced.

Inasmuch as the present invention is subject to many variations, modifications and changes in detail, it is intended that all matter described throughout this specification and shown in the accompanying drawings be interpreted as illustrative only and not in a limiting sense. Accordingly, it is intended that the invention be limited only by the spirit and scope of the hereto appended claims.

We claim:

1. A safety device to be used with a needle having a hub, comprising:
   a base having
      a first section including a protrusion and securing means surrounding said protrusion for effecting mating of said protrusion to said hub of said needle;
      a second section integrated to said first section extending away from said securing means and having means for mating with an ejection end of a syringe; and
   a housing flexibly connected to said base and pivotable toward a position in substantial alignment along the longitudinal axis of said needle for enveloping said needle, said housing further having integral locking means for fixedly retaining said needle within said housing once said housing has been pivoted to said position.

2. Safety device of claim 1, wherein said securing means comprises an annular collar having at its inner circumference threads for accepting said hub of said needle.

3. Safety device of claim 1, wherein said mating means of said second section comprises a bore extending substantially throughout said second section for slip-fittedly mating with said ejection end of said syringe.

4. Safety device of claim 1, wherein said mating means of said second section comprises means at the distal end of said second section for threadedly mating with an internally threaded collar surrounding said ejection end of said syringe.

5. Safety device of claim 1, wherein said housing comprises an elongated slot through which said needle passes when said housing is pivoted to said position.

6. Safety device of claim 1, wherein said locking means comprises a hooking means integral of said housing for securely retaining said needle within said housing.

7. Safety device of claim 1, wherein said locking means comprises a plurality of hooking means integrated into said housing for securely retaining said needle within said housing 8. Safety device of claim 1, wherein said housing is flexibly coupled to said base by a living hinge.

9. Safety device of claim 1, further comprising a substantially rigid shoulder extending from said base and to which said housing is flexibly connected.

10. Safety device of claim 1, further comprising an internal bore taperedly extending throughout said protrusion and said second section to provide a direct passage for fluid transiting between said ejection end of said syringe and said needle hub.

11. Safety device of claim 1, wherein said protrusion of said first section has a through bore substantially the size of the bore of said needle; and
   wherein said second section has a conical extension projecting away from said protrusion having a through bore substantially matching the size of the through bore of said protrusion, the respective through bores of said protrusion and said conical extension effecting one continuous through bore in said base; and
   wherein said conical extension is inserted into said ejection end of said syringe when said second section is mated to said ejection end for substantially reducing the volume of space through which fluid transits between said syringe and said needle.

12. A safety device to be used with a needle, comprising
   a base having a first end for mating with said needle and a second end for mating with a syringe; and
   a housing flexibly connected to said first end and pivotable toward a position in substantial alignment along the longitudinal length of said needle for enveloping said needle, said housing further having integral locking means for fixedly retaining said needle within said housing once said housing has been pivoted to said position.

13. Safety device of claim 12, wherein said first end comprises a male luer for mating with a hub of said needle; and
   wherein said first end further comprises an internally threaded annular collar surrounding said male luer for threading said needle hub thereto, thereby detachably coupling said needle to said first end.

14. Safety device of claim 12, wherein said second end comprises a female luer for slip-fittedly mating with an ejection end of said syringe.

15. Safety device of claim 12, wherein said second end comprises a luer locking hub for threadedly mating with an internally threaded collar surrounding an ejection end of said syringe.

16. Safety device of claim 12, wherein said locking means comprises a substantially rigid hook means integral of said housing for securely retaining said needle within said housing.

17. Safety device of claim 12, wherein said locking means comprises a plurality of hooking means integral of said housing for securely retaining said needle within said housing.

18. Safety device of claim 12, wherein said housing comprises an elongated slot through which said needle passes
   when said
   housing is pivoted to said position.

19. Safety device of claim 12, wherein said base comprises a male luer at said first end for mating to a hub of said needle;
   wherein said base further comprises a snout extending to said second end, a bore having a diameter substantially the size of that of the bore of said needle extending through said male luer and said snout;
   wherein, when said snout is inserted into an ejection end of said syringe, the fluid directly transits between said syringe and said needle through said bore extending through said male luer and said snout.

20. A safety device for a needle, comprising:

a base having
- a first section for coupling to a needle having a hub including a male projection for insertion into said hub of said needle, and an internally threaded annular collar surrounding said male projection for detachably coupling said needle via said hub;
- a second section integrally extending away from said first section including a female receptacle for accepting an ejection end of a syringe; and a housing flexibly connected to said first section of said base and pivotable to a position in substantial alignment along the longitudinal axis of said needle for enveloping said needle, said housing further having integral locking means for preventing relative movement between said needle and said housing once said housing has been pivoted to said position.

21. Safety device of claim 20, further comprising:
- a snout integrated to said second section axially positioned within said female receptacle and extending to the distal end of said second section for insertion into said ejection end of said syringe;
- a through bore having a diameter substantially the size of that of the bore of said needle extending through said male projection and said snout;
- wherein, when said snout is inserted into said ejection end of said syringe, fluid transiting between said syringe and said needle only passes through said through bore for substantially reducing the volume of space through which said fluid needs to transit.

22. Safety device of claim 20, wherein said housing comprises an elongated slot through which said needle passes when said housing is pivoted to said position.

23. Safety device of claim 20, wherein said locking means comprises a hooking means integral of said housing for securely retaining said needle within said housing.

24. Safety device of claim 20, wherein said locking means comprises a plurality of hooking means integrated into said housing for securely retaining said needle within said housing.

25. Safety device of claim 21, wherein said housing comprises an elongated slot through which said needle passes when said housing is pivoted to said position.

26. Safety device of claim 21, wherein said locking means comprises a hooking means integral of said housing for securely retaining said needle within said housing.

27. Safety device of claim 21, wherein said locking means comprises a plurality of hooking means integrated into said housing for securely retaining said needle within said housing.

* * * * *